United States Patent
Sanroma et al.

(10) Patent No.: US 10,183,289 B2
(45) Date of Patent: Jan. 22, 2019

(54) FLUID ANALYZER MANIFOLD AND TECHNIQUES

(71) Applicant: General Electric Company, Schenectady, NY (US)

(72) Inventors: John Paul Sanroma, Billerica, MA (US); Mariah Inez Hake, Lakewood, CO (US)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 15/074,537

(22) Filed: Mar. 18, 2016

(65) Prior Publication Data

US 2017/0266654 A1 Sep. 21, 2017

(51) Int. Cl.
| | | |
|---|---|---|
| *B01L 3/00* | (2006.01) | |
| *G01N 1/00* | (2006.01) | |
| *G01N 35/10* | (2006.01) | |

(52) U.S. Cl.
CPC .......... *B01L 3/502* (2013.01); *G01N 35/1095* (2013.01); *B01L 2200/026* (2013.01); *B01L 2200/12* (2013.01); *B01L 2300/0627* (2013.01); *B01L 2300/0877* (2013.01); *B01L 2300/18* (2013.01); *G01N 2001/002* (2013.01)

(58) Field of Classification Search
CPC ......... G01N 2001/002; G01N 35/1095; G01N 35/1097
See application file for complete search history.

(56) References Cited

U.S. PATENT DOCUMENTS

| 5,060,505 | A | 10/1991 | Tury et al. | |
|---|---|---|---|---|
| 5,605,179 | A | 2/1997 | Strong, Jr. et al. | |
| 8,322,232 | B1 | 12/2012 | Mayeaux | |
| 2002/0117289 | A1* | 8/2002 | Jacobs | ............... B22D 17/2038 164/338.1 |
| 2015/0177131 | A1 | 6/2015 | Liu et al. | |

OTHER PUBLICATIONS

International Search Report and Written Opinion issued in connection with corresponding PCT Application No. PCT/US2017/023132 dated Jun. 9, 2017.
Sanroma, J. P., et al., Sensor, GE Co-pending U.S. Appl. No. 29/558,581, filed Mar. 18, 2016.

* cited by examiner

*Primary Examiner* — Paul M. West
(74) *Attorney, Agent, or Firm* — Mintz Levin Cohn Ferris Glovsky and Popeo, P.C.

(57) ABSTRACT

A fluid analyzer manifold for facilitating flow of a fluid through at least one surface mounted component for analysis by a fluid analyzer. The exemplary fluid analyzer manifold can include an analysis chamber for connection with the fluid analyzer, a first flow channel having a first surface opening and a second flow channel having a second surface opening on the fluid analyzer manifold, and a mounting area on the fluid analyzer manifold. The mounting area can include the first and second surface openings of the first and second flow channels, and facilitates surface mounting the at least one surface mounted component to the fluid analyzer manifold.

7 Claims, 4 Drawing Sheets

FLUID ANALYZER MANIFOLD AND TECHNIQUES

BACKGROUND

The subject matter disclosed herein relates to fluid analyzers, such as gas analyzers. Fluid analyzers may be used to measure various properties of different types of fluids, such as liquids, gases, or mixed-phase fluids. As one example, a fluid analyzer may be used to determine the concentration of various chemical compounds in a fluid. This analysis may be used to determine whether or not the fluid meets certain acceptable process parameters, such as tolerances required during a refining or transport process.

For certain applications, continuous monitoring of a fluid is typically conducted in order to ensure that the fluid continuously conforms to required specifications. Such requirements are typically present in oil or gas pipelines or refineries, in which fluids are continually monitored to ensure proper functioning of the infrastructure. Continuous monitoring of a fluid from a pipeline may require valves and pressure regulators for allowing a specific pressure and flow rate of the fluid through the fluid analyzer. In addition, provisions may be required for so-called service gases to be sent through the analyzer for calibration or other purposes, and other components such as filters may be required or desired for a given application.

Deployment of fluid analyzers may be required in harsh conditions, for example, at temperatures as low as −40° C. in certain oil or gas pipeline applications. Further, the fluid analyzers may need to be deployed in relatively small spaces, and may need to be operable for long durations in remote areas. Typically, fluid analyzer systems are quite complex, with numerous flow components, valves, pressure regulators, and the like, required in a given deployment. Further, the system may include a fluid analyzer sensor that has a laser system and an analysis chamber. Conventionally, the fluid analyzer sensor and other components are assembled together using multiple discrete pipes, connectors, fittings, etc. Disadvantageously, a fluid analyzer system may include dozens of pipes and fittings to be connected and tested, a process which may take dozens of hours over the course of several days. In addition, each component or part of a fluid analyzer system may be prone to failure, leading to great expense and difficulty in achieving successful deployment in typical operating conditions. Therefore, enhancements to fluid analyzers and related systems to increase serviceability, reliability, ease of deployment, and decreased cost and footprint are desirable.

SUMMARY

Advantages can be provided by one or more of the embodiments disclosed herein through the provision, in one aspect, of a fluid analyzer manifold for facilitating flow of a fluid through at least one surface mounted component for analysis by a fluid analyzer. The exemplary fluid analyzer manifold can include an analysis chamber for connection with the fluid analyzer, a first flow channel having a first surface opening and a second flow channel having a second surface opening on the fluid analyzer manifold, and a mounting area on the fluid analyzer manifold. The mounting area includes the first and second surface openings of the first and second flow channels, and facilitates surface mounting the at least one surface mounted component to the fluid analyzer manifold. Advantages that may be realized in the practice of some disclosed embodiments of the fluid analyzers include increased reliability, reduced footprint, and reduced costs.

In another aspect, a fluid analyzer manifold for facilitating flow of a fluid through surface mounted components for analysis by a fluid analyzer is presented. The fluid analyzer manifold includes, for instance, an analysis chamber for connection with the fluid analyzer, and an inlet channel having an inlet opening and an outlet channel having an outlet opening on the fluid analyzer manifold, the inlet and outlet channels each being in fluid communication with the analysis chamber. In addition, the fluid analyzer may include a first flow channel comprising a first flow input opening and a first flow output opening on the fluid analyzer manifold, and a second flow channel comprising a second flow input opening and a second flow output opening on the fluid analyzer manifold. Further, the fluid analyzer may include a bypass channel comprising a bypass input opening and a bypass output opening on the fluid analyzer manifold, and a mounting area and a bypass mounting area on the fluid analyzer manifold, the mounting area including the first surface flow output opening, the second surface flow input opening, and the bypass input opening, and the bypass mounting area including the bypass output opening. The mounting area may facilitate surface mounting a first component of the surface mounted components to the fluid analyzer manifold and the bypass mounting area facilitates mounting a second component of the surface mounted components to the fluid analyzer manifold.

In a further aspect, a technique for fabricating a unibody fluid analyzer manifold from a solid bar of material is presented. For instance, an analysis chamber for connection with the fluid analyzer may be formed in the solid bar of material. In addition, the solid bar of material may be machined to form an inlet channel having an inlet opening and an outlet channel having an outlet opening on the fluid analyzer manifold. The inlet and outlet channels may each be in fluid communication with the analysis chamber. Further, the solid bar of material may be machined to form a first flow channel having a first flow input opening and a first flow output opening on the fluid analyzer manifold, a second flow channel comprising a second flow input opening and a second flow output opening on the fluid analyzer manifold, and a bypass channel having a bypass input opening and a bypass output opening on the fluid analyzer manifold. Further, the solid bar of material may be machined to form a mounting area and a bypass mounting area on the fluid analyzer manifold. The mounting area may include the first surface flow output opening, the second surface flow input opening, and the bypass input opening. The bypass mounting area may include the bypass output opening. The mounting area may facilitate surface mounting a first component of the surface mounted components to the fluid analyzer manifold and the bypass mounting area may facilitate mounting a second component of the surface mounted components to the fluid analyzer manifold.

The above embodiments are exemplary only. Other embodiments are within the scope of the disclosed subject matter.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

DETAILED DESCRIPTION

Embodiments of the disclosed subject matter provide techniques for fluid analysis, and more particularly for fluid analyzer manifolds and fabrication techniques. The present disclosure provides, in part, fluid analyzer manifolds for use in applications such continuous monitoring of fluids, as well as techniques for fabricating fluid analyzer manifolds. Advantageously, these fluid analyzer manifolds combine an analysis chamber for a fluid analyzer with facilities for connecting the fluid analyzer with a fluid source and a variety of modular surface mounted components to perform various fluidic functions such as pressure regulation, flow control, bypass, calibration, filtration, etc. As such, the fluid analyzer manifolds reduce the size and footprint required for a fluid analyzer system because the fluid analyzer manifolds include internal chambers and channels that eliminate or reduce the need for various separate parts such as tubes, pipes, fittings, etc. As a further advantage, the fluid analyzer manifolds facilitate increased reliability and ease of deployment due, in part, to the unibody designs and integrated channels and chambers provided therein. In addition, the reduction in the number of pipes, fittings, connections, etc., reduces the time required for field installation and eliminates numerous potential points of failure in the system. Other embodiments are within the scope of the disclosed subject matter.

Figure 1:
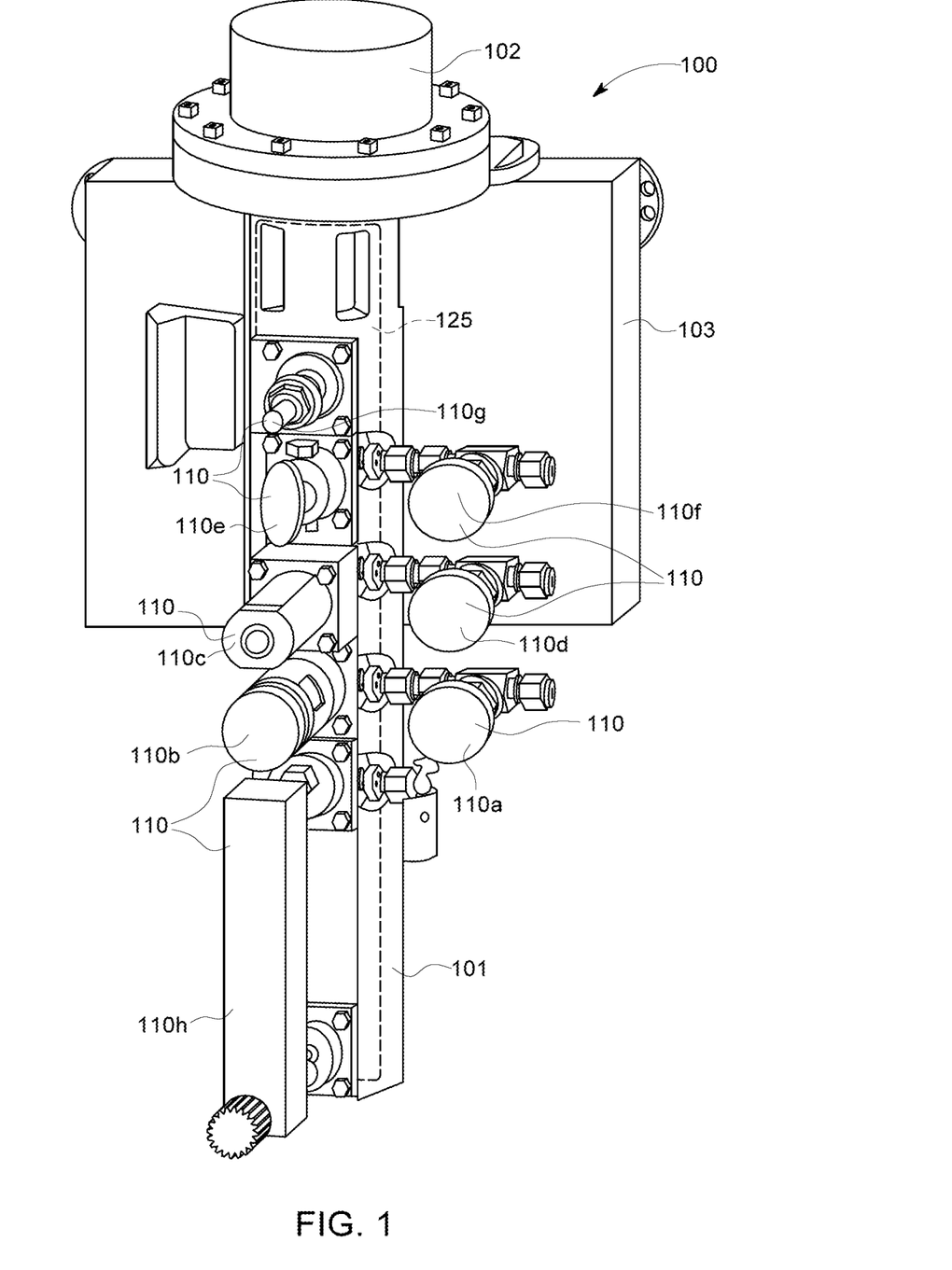
FIG. 1 depicts an exemplary fluid analyzer system having a fluid analyzer manifold, in accordance with aspects set forth herein.

FIG. 1 depicts an exemplary fluid analyzer system 100, in accordance with aspects set forth herein. In the embodiment of FIG. 1, fluid analyzer system 100 includes a fluid analyzer manifold 101, a fluid analyzer 102, and an analysis device 103. Fluid analyzer 102 may be connected to an analysis chamber 125 of the fluid analyzer manifold. In one specific example, the fluid analyzer may include tunable diode laser absorption spectroscopy (TDLAS) to measure the moisture content of a gas, such as natural gas. Fluid analyzer system 100 may further include multiple modular components 110, which may be surface mounted on fluid analyzer manifold 101. Modular components 110 may be used to provide various fluid related functions, including fluid inlets, fluid outlets, pressure regulators, filters, etc. For example, modular components 110 may include regulators or sensors, selection valves, filters, temperature sensors, rotameters, bypass valves, etc. Example supported valve types include: diaphragm, needle, toggle, pneumatic, metering, check and shut-off valves. Example supported regulator types include: back-pressure, pressure-reducing, and application options for phase changes, low pressure, or high pressure flow. Example supported filters include: filters: coalescing (membrane), high purity, and particulate. Other example components include: fittings, adapters and ports. Example sensors include: flow sensor (rotameter), pressure gauge, pressure transducer, thermometer, thermowell, and variable area flowmeter.

In one embodiment, fluid analyzer manifold 101 may be fabricated from a solid bar of metal (e.g., bar stock or billet) from which material has been removed to form various internal channels and chambers, as well as various surface mount areas. The channels, chambers, and surface mount areas of fluid analyzer manifold 101 allow connection of modular components 110 and fluid analyzer 102. The internal channels and chambers of fluid analyzer manifold 101 may allow a fluid to pass through fluid analyzer system 100 in a regulated manner to facilitate accurate fluid analysis. Advantageously, the unibody construction of fluid analyzer manifold 101 may allow for the elimination of numerous tubes, pipes, fittings, seals, connectors, etc., thus reducing the number of components which may potentially fail in fluid analyzer system 100, therefore increasing reliability. As another advantage, overall system size and installation complexity may be reduced, allowing more flexible field deployment options. As a further advantage, a unibody construction in which a solid bar of metal has been machined to form the various channels and surface mount areas may allow for greater fluid pressure to be handled by the system.

The embodiment of FIG. 1 illustrates one exemplary flow path through fluid analyzer system 100. For instance, first a fluid may be connected to a supply fluid valve component 110a. Next, the fluid may flow within fluid analyzer manifold 101 to a membrane filter component 110b, which may be designed to remove impurities to protect fluid analyzer 102. For example, membrane filter component 110b may be used to remove small amounts of liquid present in a gas on a continuous basis. For example, filter component 110b may serve one or more purposes. One purpose may be to protect other modular components 110, e.g., the rotameter, which are sensitive to impurities. Another purpose is to help filter the gas for users of the fluid analyzer system 100. Advantageously, filtering in the continuous fluid analyzer may improves gas product quality without requiring a separate deployment. A further purpose may be to mitigate blockage in the system, due to impurities collecting in flow channels. In another embodiment, a wedge window may be provided to separate the fluid analyzer from the sampling region, so that the fluid analyzer components are not directly exposed to the gas.

Next, the fluid may travel within fluid analyzer manifold 101 to a pressure regulator component 110c, which may be used to adjust the pressure of the fluid to ensure that an appropriate target fluid pressure continues within fluid analyzer system 100 for analysis by fluid analyzer 102.

Continuing with the exemplary flow path, the fluid may flow within fluid analyzer manifold 101 from pressure regulator component 110c towards both a bypass valve component 110*d* and a selection valve component 110*e*. In such a case, some fluid may be allowed to exit fluid analyzer system 100 at bypass valve component 110*d*, e.g., to reduce the amount of fluid in fluid analyzer system 100 to facilitate faster analysis. Then, the rest of the fluid may flow within fluid analyzer manifold 101 towards selection valve component 110*e*.

Next, selection valve component 110*e* may be connected to a service fluid valve component 110*f* and a sample fluid valve component 110*g*. Selection valve component 110*e* may therefore select whether the fluid under test from pressure regulator component 110*c*, or a service fluid from service fluid valve component 110*f*, may flow to sample fluid valve component 110*g*. For example, a service fluid may be used to calibrate the system. The selected fluid may flow within fluid analyzer manifold 101 from sample fluid valve component 110*g* to analysis chamber 125. Sample fluid valve component 110*g* may be used to fine-tune the pressure or amount of fluid entering analysis chamber 125.

In addition, once the fluid enters analysis chamber 125, the fluid may be analyzed by fluid analyzer 102, and the results of the analysis may be sent to analysis device 103. Analysis device 103 may also receive signals from any or all of components 110. Next, the fluid may flow through fluid analyzer manifold 101 to a rotameter component 110*h* which may calculate the fluid flow rate. The fluid may subsequently exit fluid analyzer system 100, and enter the next phase of a customer process.

In various embodiments, the multiple components 110, which may be surface mounted to fluid analyzer manifold 101, may comprise any of the components noted above, e.g., supply fluid valve component 110*a*, membrane filter component 110*b*, pressure regulator component 110*c*, bypass valve component 110*d*, selection valve component 110*e*, service fluid valve component 110*f*, sample fluid valve component 110*g*, rotameter component 110*h*, and the like. Depending upon a specific application, different components 110 may be surface mounted in different orders or configurations to fluid analyzer manifold 101. In the descriptions that follow, for ease of comprehension a similar nomenclature will be used, and a suffix letter will identify the location of an element in correspondence with the suffixes a-h, etc., as used above with respect to components 110*a*-110*h*.

By way of overview of the operation of fluid analyzer system 100, signals from fluid analyzer 102 may be sent to analysis device 103 via electronic connections. Advantageously, the integrated design of fluid analyzer system 100 allows for the elimination of a junction box, which would otherwise be mounted to fluid analyzer manifold 101. Instead of using a junction box, the electronics and electrical connections may be housed directly within the analyzer through a back portion of fluid analyzer manifold 101, allowing for elimination of a separate junction box, reducing bulk and further connection points that may fail. In addition, analysis device 103 may also capture signals from various sensors, such as sensors integrated within components 110. These sensors may include pressure sensors, temperature sensors, etc. Analysis device 103 may combine the input from fluid analyzer 102 and other sensors, such as components 110, in performing fluid analysis functions.

For example, analysis device 103 may combine such information to determine the number of parts per million (PPM) of moisture in the sample fluid, and analysis device 103 may display such information on a user interface of a connected screen or other output device. In addition, analysis device 103 may obtain sensor information from rotameter component 110*h*, and display such information on the user interface as an indication that fluid analyzer system 100 is functioning properly and that an appropriate amount of fluid is passing through to facilitate meaningful analysis.

As one having ordinary skill in the art will readily understand, in one specific example, fluid analyzer 102 may include a tunable diode laser absorption spectroscopy (TDLAS) system. A TDLAS moisture analyzer may be used to determine the moisture content of a fluid. At certain specific frequencies, light energy will be absorbed by water molecules. As the concentration of water increases, the absorption also increases. A TDLAS fluid analyzer can sweep a diode laser output through a narrow spectrum of light frequencies. By measuring the return light intensity with a photo detector as compared to the incident light intensity, the fluid analyzer can provide a direct indication of the partial pressure of water. The partial pressure divided by the total pressure yields the mole ratio, which may be expressed as parts per million by volume (ppmv).

Fluid analyzer manifolds as disclosed herein may be used in a variety of applications. For instance, many applications, such as petrochemical application, require the measurement or control of fluid composition and properties, and a fluid analyzer manifold can facilitate integration of such measurement and composition control devices with the fluid source. In addition, ultrasonic flowmeters, which measure mass flow rate of a liquid or gas, may use ultrasonic transducers to conserve energy and reduce fluid loss by identifying sources of leaks into flare systems. In such a case, the ultrasonic transducers may be integrated with fluid analyzer manifold 101 to provide a complete system.

Various structural features of exemplary fluid analyzer manifold 101 facilitate the fluid analysis examples described with respect to FIG. 1. For instance, fluid analyzer manifold 101 includes surface openings to facilitate surface mounting of components, as well as internal chambers and channel to facilitate fluid flow between and among the components. Regarding surface features, FIGS. 2A-2C are elevational views of the front, right side, and left side, respectively, of fluid analyzer manifold 101, in accordance with aspects set forth herein.

Figure 2A:
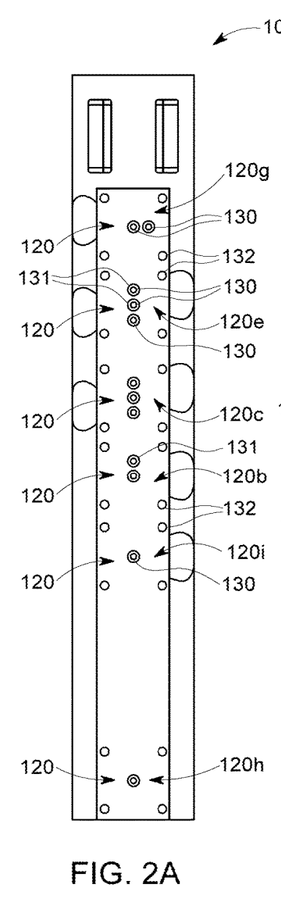
FIG. 2A is an elevational view of the front of the fluid analyzer manifold of FIG. 1, in accordance with aspects set forth herein.
Figures 2B, 2C:
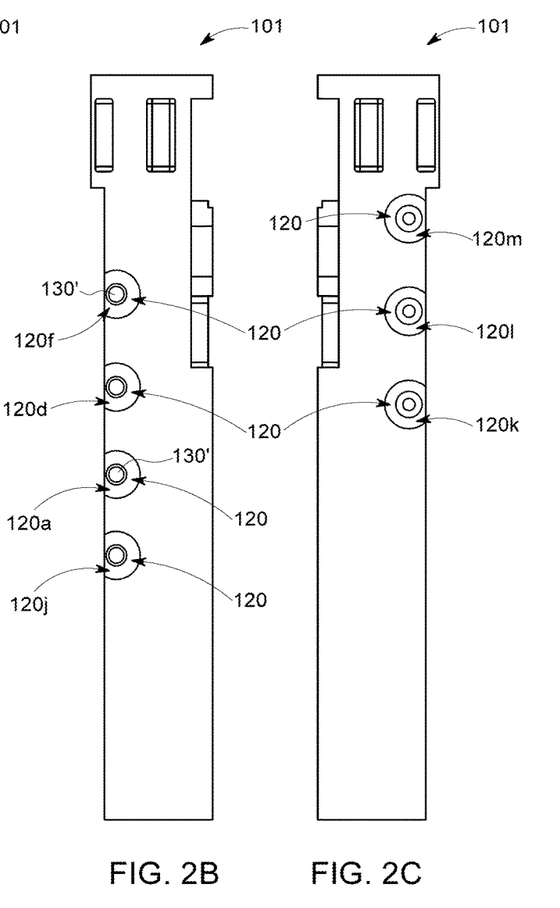
FIG. 2B is an elevational view of the right side of the fluid analyzer manifold of FIG. 1, in accordance with aspects set forth herein.
FIG. 2C is an elevational view of the left side of the fluid analyzer manifold of FIG. 1, in accordance with aspects set forth herein.

In the embodiment of FIGS. 2A-2C, fluid analyzer manifold 101 includes numerous surface mounting areas 120. Surface mounting areas 120 may comprise surface mounting areas 120*a*-120*m*, and may facilitate surface mounting of components 110*a*-110*h* (see FIG. 1) to the different surfaces of fluid analyzer manifold 101.

Characterizations of components 110 and mounting areas 120 as set forth herein in one embodiment are summarized with reference to Table 1.

TABLE 1

| Components | Mounting Areas |
| --- | --- |
| supply fluid valve component 110a | mounting area 120a |
| membrane filter component 110b | mounting area 120b |
| pressure regulator component 110c | mounting area 120c |
| bypass valve component 110d | mounting area 120d |
| selection valve component 110e | mounting area 120e |
| service fluid valve component 110f | mounting area 120f |
| sample fluid valve component 110g | mounting area 12g |
| rotameter component 110h | mounting areas 120h, 120i |

Various types of surface mounting areas may be defined to support the requirements of various types of surface mounted components 110. For instance, some surface mounting areas 120, such as surface mounting areas 120*b*, 120*c*, 120*e*, 120*g*-120*i*, may include one or more surface openings 130 of fluid analyzer manifold 101, as well as multiple (e.g., four) threaded holes 132 that allow components 110 to be fastened to the surface of fluid analyzer manifold 101. Openings 130 may be surrounded by O-ring grooves 131 to facilitate fluid-tight sealing of components 110 to the surface of fluid analyzer manifold 101. In such a case, a component 110 may be mounted over a surface mounting area 120 with access to multiple surface openings 130 to facilitate a fluid flowing from one opening 130 to other openings 130, after component 110 performs its fluidic function, e.g., pressure regulation, filtration, etc.

In addition, other surface mounting areas 120, such as surface mounting areas 120a, 120d, 120f, and 120j, may include a single threaded tapered opening 130', to which another style of component 110 may be mounted directly without being bolted to fluid analyzer manifold 101 using threaded holes 132. For example, threaded tapered opening 130' may conform to an American Society of Mechanical Engineers (ASME) National Pipe Thread Taper (NPT) standard. Further surface mount areas 120, such as surface mounting areas 120k-120m may be provided which include openings that are aligned perpendicular to the axis of the longitudinal flow channels to allow for separation of a single longitudinal channel into multiple distinct flow channel through the use of different types of plugs 145 of FIG. 2E, which will be further explained below.

Figure 2D:
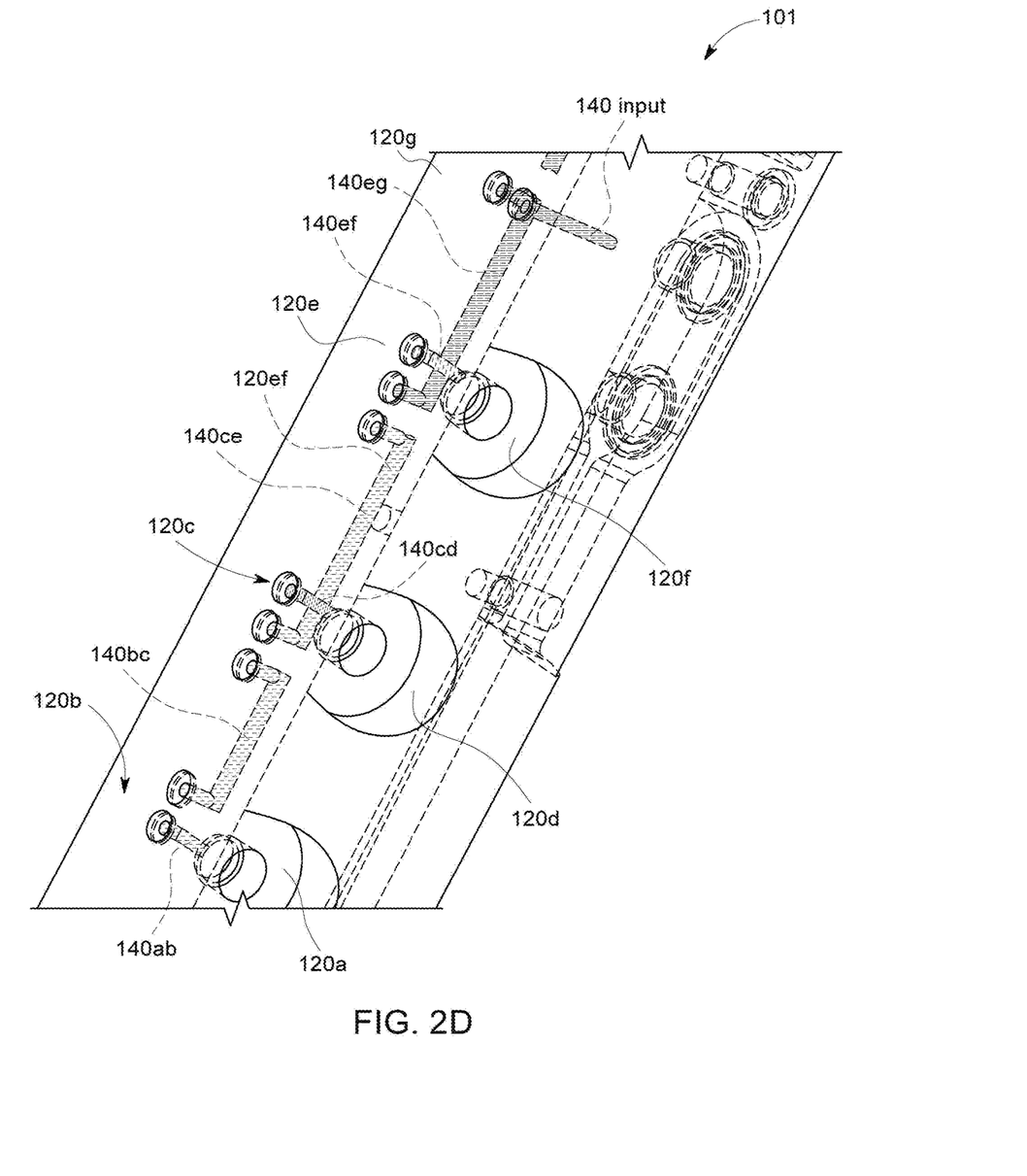
FIG. 2D is a partially transparent detailed view of a middle portion of the fluid analyzer manifold of FIG. 1, in accordance with aspects set forth herein.
Figure 2E:
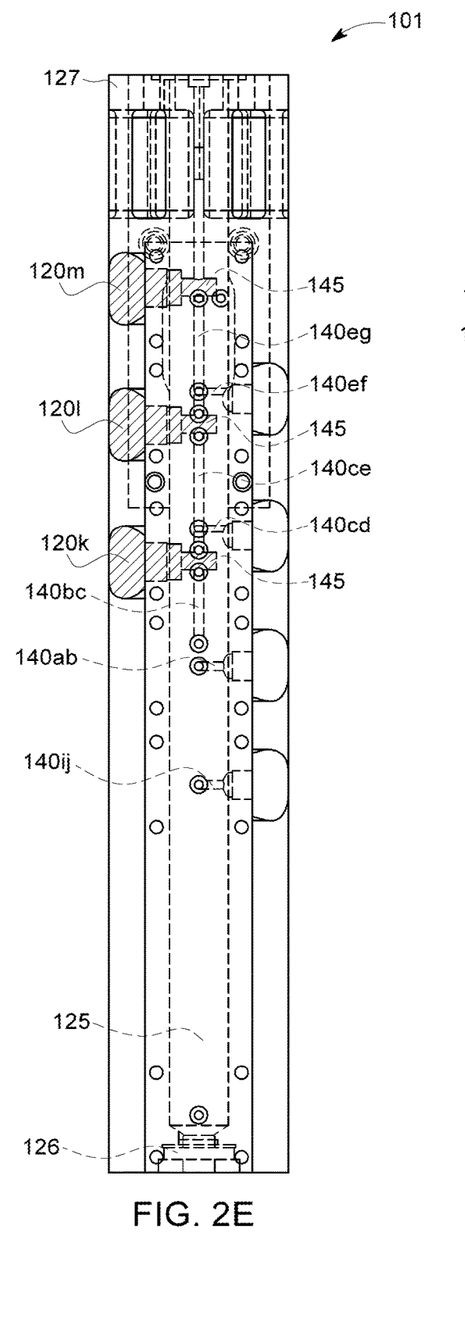
FIG. 2E is a partially transparent view of the front of the fluid analyzer manifold of FIG. 1, in accordance with aspects set forth herein.
Figure 2F:
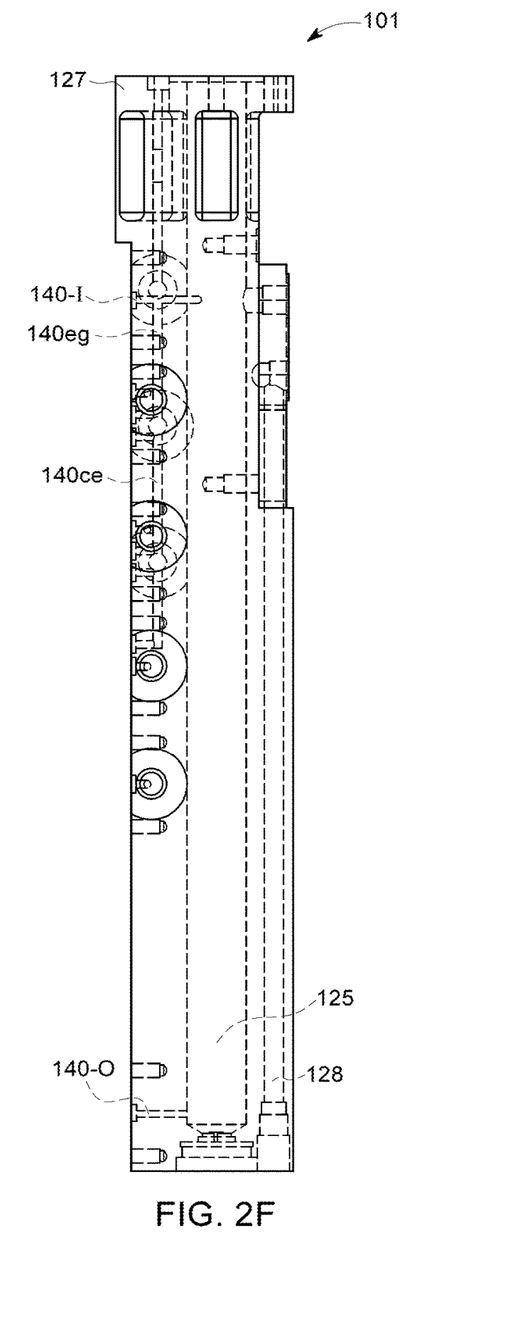
FIG. 2F is a partially transparent view of the right side of the fluid analyzer manifold of FIG. 1, in accordance with aspects set forth herein.

Turning next to the internal features, FIG. 2D-2F are partially transparent views of fluid analyzer manifold 101, in accordance with aspects set forth herein. Various flow channels 140 may be seen in the transparent view of FIG. 2D, and may be described with respect to which surface mount areas 120 are joined by flow channels 140. In addition, six different flow channels 140 are depicted. Further, some flow channels are substantially U-shaped, other flow channels are substantially L-shaped, and yet other flow channels are substantially straight. In other embodiments, the flow channels may have other shapes, such as I-shaped or T-shaped channels, or may be angled, such as having a V-shape instead of an L-shape, or may be more rounded, or may be offset from one another to accommodate many different flow channels which are located within close proximity.

To understand how the various flow channels may be employed, the embodiment of FIG. 2D depicts multiple types of mounting areas 120, which may include one, two, or three openings 130, 130'. Such configurations allow for different types of components 110 to facilitate the flow of the fluid within fluid analyzer manifold 101 to achieve continuous monitoring of the fluid. For example, mounting areas 120c, 120e may be viewed as bypass mounting areas, because each mounting area includes three different openings 130 of three different flow channels 140. In such a case, an appropriate component 110 may allow change of fluid flow depending on conditions.

For example, selection valve component 110e (FIG. 1) may be mounted to mount area 120e, which includes openings 130 of flow channels 140ce, 140ef, and 140eg. In such a case, selection valve component 110e may be configured to allow fluid to flow either from flow channel 140ce to flow channel 140eg, to facilitate fluid analysis. Alternately, selection valve component 110e may be configured to restrict flow from flow channel 140ce and allow fluid to flow from flow channel 140ef to flow channel 140eg, to facilitate the use of a service gas in calibrating the fluid analysis system. In an analogous manner, each of the mounting areas may be used, with an appropriate component, such as a flow component, to direct fluid flow to any of the included flow channels that have openings at the mounting area. For example, characterizations of flow channels 140 and connections as set forth herein in one embodiment are summarized with reference to Table 2.

TABLE 2

| Flow Channel | Shape | Connections | Components |
|---|---|---|---|
| flow channel 140ab | L-shaped | mounting areas 120a, 120b | supply fluid valve component 110a, membrane filter component 110b |
| flow channel 140bc | U-shaped | mounting areas 120b, 120c | membrane filter component 110b, pressure regulator component 110c |
| flow channel 140cd | L-shaped | mounting areas 120c, 120d | pressure regulator component 110c, bypass valve component 110d |
| flow channel 140ce | U-shaped | mounting areas 120c, 120e | pressure regulator component 110c, selection valve component 110e |
| flow channel 140ef | L-shaped | mounting areas 120e, 120f | selection valve component 110e |
| flow channel 140eg | U-shaped | mounting areas 120e, 120g | service fluid valve component 110f |
| flow channel 140-I | Straight | mounting area 120g, analysis chamber 125 | sample fluid valve component 110g, fluid analyzer 102 |
| flow channel 140-O | Straight | analysis chamber 125, mounting area 120h | fluid analyzer 102, rotameter component 110h |
| flow channel 140ij | L-shaped | mounting areas 120i, 120j | rotameter component 110h, fluid outlet valve (not shown) |

Returning to internal features, FIGS. 2E & 2F are partially transparent views of the front side and the right side, respectively, of fluid analyzer manifold 101, in accordance with aspects set forth herein. As compared with FIGS. 2A & 2F, internal channels and chambers of fluid analyzer manifold 101 are depicted.

Regarding fabrication methods and techniques, in order to fabricate flow channels 140, deep hole formation techniques, such as gundrilling, may be employed. For example, in one embodiment, fluid analyzer manifold may include channels that have an aspect ratio, e.g., ratio of length to diameter, of up to 400:1, the formation of which may not be feasible using certain drilling techniques. In one example, a cutting process may be employed in which a cutting tool is provided with a mechanism for delivering coolant to the tip of a drill, so that the chips are removed from the hole to facilitate the formation of a straight, deep hole. In the illustrated embodiment, surface mounting areas 120k-120m allow for the provision of plugs 145 to separate a single longitudinally drilled flow channel into multiple flow channels 140, in order to achieve U-shaped flow channels. Other style plugs may be used so that a flow channel is not fully blocked by the plug, such as a situation in which it is desired for the plug to direct flow into an appropriate channel.

In one embodiment of a process for forming fluid analyzer manifold 101, a solid bar of material, such as metal bar stock, may be obtained and machined, using gundrilling or other deep hole formation techniques, to form flow channels 140, surface openings 130, etc. In addition, other machining techniques may be used to form the other external and internal features of fluid analyzer manifold 101, including threaded holes 132 and tapered openings 130'. Advantageously, the formation of fluid analyzer manifold 101, starting from a solid block of metal, eliminates the possibility that numerous parts such as tubes, pipes, fittings, flanges, etc., may be incorrectly assembled when a fluid analyzer system is deployed, because the connections are made during the fabrication process which may be carefully controlled and monitored. As another advantage, fluid analyzer manifolds 101 may be readily mass produced. In another embodiment, an additive manufacturing process (e.g., 3D printing) may be used to form fluid analyzer manifold 101. For example, successive layers of metal or a metal alloy may be formed using an appropriate controller to create fluid analyzer manifold 101.

In the embodiment of FIGS. 2E & 2F, fluid analyzer manifold 101 includes an analysis chamber 125. For example, analysis chamber 125 may be connected to a bottom mounting area 126 and a top mounting area 127, which may be used to mount fluid analyzer 102 (see FIG. 1) to fluid analyzer manifold 101. For example, a TDLAS system may be provided by mounting a laser source to top mounting area 127 and a mirror component to bottom mounting area 126. In other applications, fluid analyzer manifold 101 may be configured with application-dependent mounting areas, application-dependent flow channels, and one or more application-dependent analysis chambers. In such a case, the chambers and/or flow channels may be configured to facilitate connection with the appropriate sensors, to accommodate access of the fluid analyzer and sensors thereof to the sampling region or analysis chambers.

In an additional embodiment, fluid analyzer manifold 101 may include an input flow channel 140-I and an output flow channel 140-O. In the embodiment of FIG. 2F, for example, flow channels 140-I, 140-O may be in fluid communication with analysis chamber 125.

In a further embodiment, fluid analyzer manifold 101 may include a heating channel 128, which is not in fluid communication with the analysis chamber 125. For instance, heating channel 128 may be spaced apart from analysis chamber 125, and may extend for a majority of the length thereof. In addition, heating channel 128 may allow for the provision of a heater. In such a case, because of the unibody metal construction of fluid analyzer manifold 101, heat from the heater may readily conduct throughout fluid analyzer manifold 101, and transfer to the fluid being analyzed. For example, the heater may uniformly heat the fluid within analysis chamber 125 because of the disposition of heating channel 128 along analysis chamber 125. Advantageously, by allowing for all fluid connections to be made by flow channels 140, which are within fluid analyzer manifold 101, a heater deployed in heating channel 128 may allow for a fluid analyzer system to be installed in harsh conditions, such as temperatures that range below −40° C. For example, a ⅛" diameter electric cartridge heater may be deployed within heating channel 128. Depending upon the requirements, the metal or metal alloy of fluid analyzer manifold 101 may be selected to provide appropriate thermal conductivity to facilitate the heating functionality. For example, in one specific embodiment, fluid analyzer manifold may be formed from stainless steel, so that the manifold has the required strength and anti-corrosion properties needed for deployment with sample fluids.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fluid analyzer manifold for facilitating flow of a fluid through surface mounted components for analysis by a fluid analyzer, the fluid analyzer manifold comprising:
   an analysis chamber for connection with the fluid analyzer;
   an inlet channel having an inlet opening and an outlet channel having an outlet opening on the fluid analyzer manifold, the inlet and outlet channels each being in fluid communication with the analysis chamber;
   a first flow channel comprising a first flow input opening and a first flow output opening on the fluid analyzer manifold;
   a second flow channel comprising a second flow input opening and a second flow output opening on the fluid analyzer manifold;
   a bypass channel comprising a bypass input opening and a bypass output opening on the fluid analyzer manifold; and
   a mounting area and a bypass mounting area on the fluid analyzer manifold, the mounting area including the first surface flow output opening, the second surface flow input opening, and the bypass input opening, and the bypass mounting area including the bypass output opening, wherein the mounting area facilitates surface mounting a first component of the surface mounted components to the fluid analyzer manifold and the bypass mounting area facilitates mounting a second component of the surface mounted components to the fluid analyzer manifold;
   wherein the first flow channel extends transverse to the second flow channel and the at least one surface mounted component facilitates a transverse change in direction of the flow of the fluid from one of the first or second flow channels to the other of the first or second flow channels.

2. The fluid analyzer manifold of claim 1, further comprising an inlet mounting area on the fluid analyzer manifold, the inlet mounting area including the inlet opening and the first surface flow input opening, wherein the inlet mounting area facilitates surface mounting a third component of the surface mounted components to the fluid analyzer manifold.

3. The fluid analyzer manifold of claim 2, further comprising an outlet mounting area on the fluid analyzer manifold, the outlet mounting area including the outlet opening and the second surface flow output opening, wherein the outlet mounting area facilitates surface mounting a fourth component of the surface mounted components to the fluid analyzer manifold.

4. The fluid analyzer manifold of claim 1, further comprising an outlet mounting area on the fluid analyzer manifold, the outlet mounting area including the outlet opening and the second surface flow output opening, wherein the outlet mounting area facilitates surface mounting a third component of the surface mounted components to the fluid analyzer manifold.

5. The fluid analyzer manifold of claim 1, further comprising a heating channel spaced apart from the analysis chamber, the heating channel configured to receive a heater for heating the fluid during the analysis.

6. The fluid analyzer manifold of claim 1, further comprising a fluid analyzer mounting portion configured to connect the fluid analyzer to the analysis chamber.

7. The fluid analyzer manifold of claim 1, wherein the first and second flow channels are gundrilled flow channels.

* * * * *